United States Patent [19]

Fischer et al.

[11] 4,413,149
[45] Nov. 1, 1983

[54] PROCESS FOR THE CATALYTIC HYDROGENOLYSIS OF P-SUBSTITUTED BENZALDEHYDE-DIMETHYLACETALS TO PRODUCE THE CORRESPONDING BENZYL METHYL ETHER DERIVATIVES

[75] Inventors: Hartmut Fischer, Hofheim; Detlef H. Skaletz, Mainz, both of Fed. Rep. of Germany

[73] Assignee: Hoechst Aktiengesellschaft, Frankfurt am Main, Fed. Rep. of Germany

[21] Appl. No.: 333,012

[22] Filed: Dec. 21, 1981

[30] Foreign Application Priority Data

Dec. 24, 1980 [DE] Fed. Rep. of Germany ....... 3048993

[51] Int. Cl.³ .................. C07C 43/205; C07C 41/28
[52] U.S. Cl. .............................. 568/636; 568/644; 568/648; 568/592; 502/161
[58] Field of Search ................ 568/636, 660, 648, 644

[56] References Cited

U.S. PATENT DOCUMENTS 4,201,868  5/1980  Slinkard .............................. 560/232

OTHER PUBLICATIONS

Fleming et al., Canadian Jour. of Chem., vol. 54 (1976), 685–694.
Rylander, Paul N., "Catalytic Hydrogenation Over Platinum Metals" 1967, pp. 449–454.
Fleming, Bruce and Bolker, Henry, "The Reduction of Acetals with Cobalt Carbonyl Catalysts", Aug. 1975, pp. 685–693.
Wender, Irving and Pino, Piero, "Organic Synthesis via Metal Carbonyls", 1968, pp. 84–86.
Slaugh, Lynn H. and Mullineaux, Richard D, "Novel Hydroformylation* Catalysts", Feb. 1968, pp. 469–477.
Forester, Denis and Roth, James F., "Homogeneous Catalysts-II" Aug. 1973, pp. 27–31.

Primary Examiner—Bernard Helfin
Attorney, Agent, or Firm—Schwartz, Jeffery, Schwaab, Mack, Blumenthal & Koch

[57] ABSTRACT

Disclosed is a process for catalytic hydrogenolysis of p-substituted benzaldehyde-dialkyl-acetals of the general formula

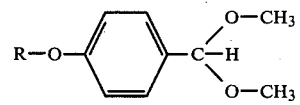

in which R is an alkyl group, an unsubstituted or substituted aryl group or an unsubstituted or substituted aralkyl group, by means of a catalyst system composed of cobalt carbonyl and at least one nitrogen-containing heterocyclic compound, such as pyridine, pyrrole, pyrrolidone or piperidine and a hydrogen/carbon monoxide mixture to give the corresponding p-substituted benzyl alkyl ether derivatives.

5 Claims, No Drawings

PROCESS FOR THE CATALYTIC HYDROGENOLYSIS OF P-SUBSTITUTED BENZALDEHYDE-DIMETHYLACETALS TO PRODUCE THE CORRESPONDING BENZYL METHYL ETHER DERIVATIVES

BACKGROUND OF THE INVENTION

The present invention relates to a process for the catalytic hydrogenolysis of p-substituted benzaldehydedialkylacetals to give the corresponding p-substituted benzyl alkyl ether derivatives.

The hydrogenolysis of benzaldehyde-dialkylacetals is known and leads to toluene, with elimination of both the alkoxy groups. This reaction takes place almost quantitatively, if the hydrogenolysis is carried out with palladium or platinum catalysts. This reaction is used, for example, when a benzyl radical which has been introduced as a protective group into a molecule is to be selectively removed again from the molecule (in this context, see, for example, P. N. Rylander, *Catalytic Hydrogenation over Platinum Metals*, Academic Press-New York and London, 1967, pages 449 to 454).

The catalysts of the benzyl cleavage are, however, completely unsuitable for eliminating only one methoxy radical from the dimethylacetal of benzaldehyde, in order to synthesize the corresponding benzyl methyl ether. It is known, however, from the state of the art to hydrogenolyze benzaldehyde-dialkylacetals to produce benzyl alkyl ethers by using cobalt carbonyl as the catalyst and reacting the acetals with a mixture of carbon monoxide and hydrogen. For example, in an article entitled "The reduction of acetals with cobalt carbonyl catalysts" in *Can. J. Chem.*, Volume 54, 1976, pages 685 to 694, B. I. Fleming and H. I. Bolker describe the reaction of benzaldehyde-dimethylacetal (IIa), benzaldehyde-dibenzylacetal (IIb) and the p-substituted compounds 4-methoxybenzaldehyde-dibenzylacetal (IIc) and 4-chloro-benzaldehyde-dibenzylacetal (IId)

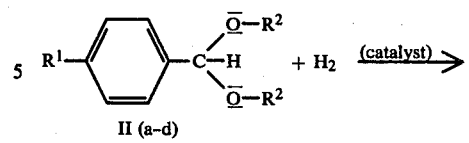

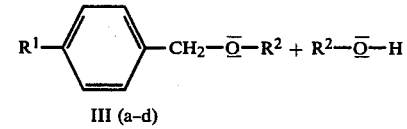

| Reactant | $R^1$ | $R^2$ | Product |
|---|---|---|---|
| IIa | H | $CH_3$ | IIIa |
| b | H | $CH_2$—⟨phenyl⟩ | b |
| c | $\bar{O}$—$CH_3$ | $CH_2$—⟨phenyl⟩ | c |
| d | Cl | $CH_2$—⟨phenyl⟩ | d | to give the benzyl methyl ether (IIIa) in 96% yield, the dibenzyl ether (IIIb) in 95% yield, the (4-methoxybenzyl) benzyl ether (IIIc) in 59% yield and the (4-chlorobenzyl) benzyl ether (IIId) in 16% yield. The catalyst used is $Co_2(CO)_8$ in benzene, and the ratio of $H_2$ to CO is 2 to 1.

When this known process is transferred to those dimethylacetals of benzaldehydes which have an alkoxy, aryloxy or aralkoxy group in the p-position, for example, to 4-methoxy-benzaldehyde-dimethyl acetal or to 4-phenoxy-benzaldehyde-dimethylacetal, this catalytic hydrogenolysis proceeds only with low selectivity. Thus, in the hydrogenolysis of 4-methoxy-benzaldehyde-dimethylacetal (IV) with cobalt carbonyl as the catalyst, only about 10 to 12% of 4-methoxybenzyl methyl ether (Va) is obtained. As further products, 4-methoxytoluene (Vb) and (4-methoxy-phenyl)-acetaldehyde-dimethylacetal (Vc) are formed in yields of about 49 and 40% respectively:

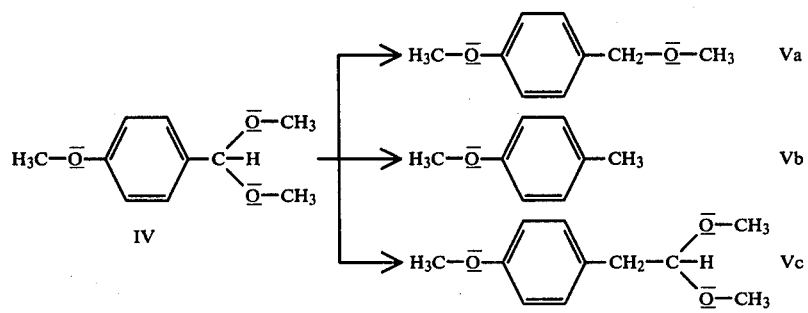

It may be assumed that compound (Vb) is formed from (IV) by "benzyl ether" cleavage and compound (Vc) is formed by insertion of carbon monoxide into the acetal group, the chain being lengthened by one $CH_2$ group by subsequent hydrogenation.

The bis-dimethylacetal of 4,4'-diphenyl etherdialdehyde (VI) which is described for the first time in German patent application No. 30 48 992.0, corresponding to U.S. application Ser. No. 333,013 filed concurrently herewith and having the title "4,4'-Diphenyl Ether-Dialdehydebis-Dimethylacetal and a Process For Its Preparation", shows a very similar behavior. In the hydrogenolysis carried out analogously to B. I. Fleming et al. (cited above), 26% of 4,4'-bis-(methoxy-methyl)-diphenyl ether (VII) are obtained, while the benzyl ether cleavage proceeds to the extent of 16% and the insertion of carbon monoxide proceeds to the extent of 20%. In addition, several further unknown products are formed, so that the course of the hydrogenolysis of the compound (VI) under known process conditions is markedly unselective.

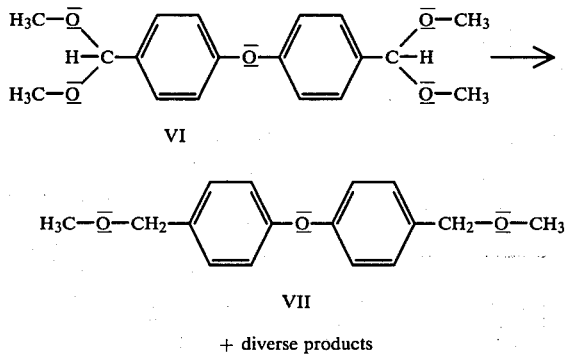

+ diverse products

Modifications of cobalt carbonyl catalysts which lead to very diverse results have also been previously described in the literature:

For example, it is stated in *Organic Syntheses via Metal Carbonyls*, edited by I. Wender and P. Pino, Interscience Publishers-New York, 1968, pages 84 to 86, that bases acting on cobalt carbonyl initiate the disproportionation of the latter to give ionic complexes, and this is also termed the "base reaction". In this way, the cobalt carbonyl, as a catalytically active compound of a homogeneous reaction system, can be transformed into inactive ion pairs.

In the articles "Novel Hydroformylation Catalysts" by L. H. Slaugh and R. D. Mullineaux in *J. Organometal. Chem.*, Vol. 13, 1968, pp. 469–477, and "Homogeneous Hydrogenation of Ketones Catalyzed by Cobalt Carbonyl Phosphine Complexes" by L. Marko, B. Beil and S. Vastag in *Homogeneous Catalysis-II, Advances in Chemistry Series* 132 of the American Chemical Society, 1974 pp. 27–32, it is suggested, in order to control the selectivity of cobalt carbonyl catalysts, to modify the latter with certain organic phosphorus compounds. This known method, however, fails when used in the hydrogenolysis of the acetals indicated at the outset. It was not possible to achieve a hydrogenolysis of these acetals with cobalt carbonyls which contained triphenylphosphane, tri-n-butylphosphane or triethyl phosphite.

SUMMARY OF THE INVENTION

It is therefore an object of the present invention to provide an improved process for the catalytic hydrogenolysis of p-substituted benzaldehyde-dialkylacetals to produce the corresponding p-substituted benzyl alkyl ether derivatives.

Another object of the invention is to provide a catalyst system which enables certain p-substituted benzaldehyde-dimethylacetals to be transformed with a relatively high selectivity into the corresponding benzyl methyl ethers.

In accomplishing the foregoing objects, there has been provided in accordance with the present invention a process for the catalytic hydrogenolysis of p-substituted benzaldehyde-dialkylacetals to produce the corresponding p-substituted benzyl alkyl ether derivative, comprising the step of hydrogenolyzing a p-substituted benzaldehydedialkylacetal compound of the formula

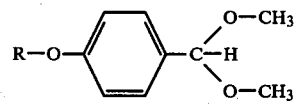

wherein R is an alkyl group, an unsubstituted or substituted aryl group, or an unsubstituted or substituted aralkyl group, in the presence of a catalyst system comprising a cobalt carbonyl and at least one heterocyclic compound containing at least one heterocyclic nitrogen atom. Preferably, the alkyl group contains 1 to 4 carbon atoms and the aryl group comprises phenyl. The most preferred benzaldehyde-dialkylacetal starting compounds are 4-methoxy-benzaldehyde-dimethylacetal, 4-phenoxy-benzaldehyde-dimethylacetal, and 4,4'-diphenyl ether-dialdehyde-bis-dimethylacetal. The preferred nitrogen-containing heterocyclic compounds comprise five or six-membered heterocyclic compounds with one heterocyclic nitrogen atom. The most preferred heterocyclic compounds are pyridine, pyrrole, pyrrolidone and piperidine. The terms "substituted aryl" and "substituted aralkyl" comprise aryl and aralkyl groups which have alkyl substituents comprising C, H and/or O atoms.

Further objects, features and advantages of the present invention will become apparent from the detailed description of preferred embodiments which follows.

DETAILED DESCRIPTION OF PREFERRED EMBODIMENTS

The invention proceeds from the known process for the catalytic hydrogenolysis of p-substituted benzaldehyde-dialkylacetals by means of a cobalt carbonyl catalyst and a hydrogen/carbon monoxide mixture to give the corresponding p-substituted benzyl alkyl ether derivatives. The process according to the invention then comprises hydrogenolyzing compounds of the general formula (I)

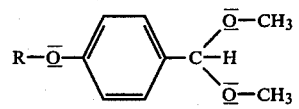

in which R is an alkyl group, an unsubstituted or substituted aryl group or an unsubstituted or substituted aralkyl group, by means of a catalyst system composed of cobalt carbonyl and at least one nitrogen-containing heterocyclic compound. The starting materials which can be used in this process are, in particular, those in which the alkyl group contains 1 to 4 C atoms and the aryl group is phenyl. The following are mentioned as examples:

4-methoxy-benzaldehyde-dimethylacetal (Ia), 4-ethoxy-benzaldehyde-dimethylacetal (Ib),
4-phenoxy-benzaldehyde-dimethylacetal (Ic),
4-benzyloxy-benzaldehyde-dimethylacetal (Id), and
4,4′-diphenyl ether-dialdehyde-bis-dimethylacetal (Ie=VI).

These starting materials can be prepared by procedures known in the art, e.g., as described in German Offenlegungsschrift No. 2,848,397, the disclosure of which is hereby incorporated by reference.

The corresponding principal products of the reaction then are:

(4-methoxy-benzyl) methyl ether (VIIIa),
(4-ethoxy-benzyl) methyl ether (VIIIb),
(4-phenoxy-benzyl) methyl ether (VIIIc),
(4-benzyloxy-benzyl) methyl ether (VIIId), and
4,4′-bis-(methoxymethyl)-diphenyl ether (VIIIe=VII).

For these examples, the reaction can be represented by the following general equation:

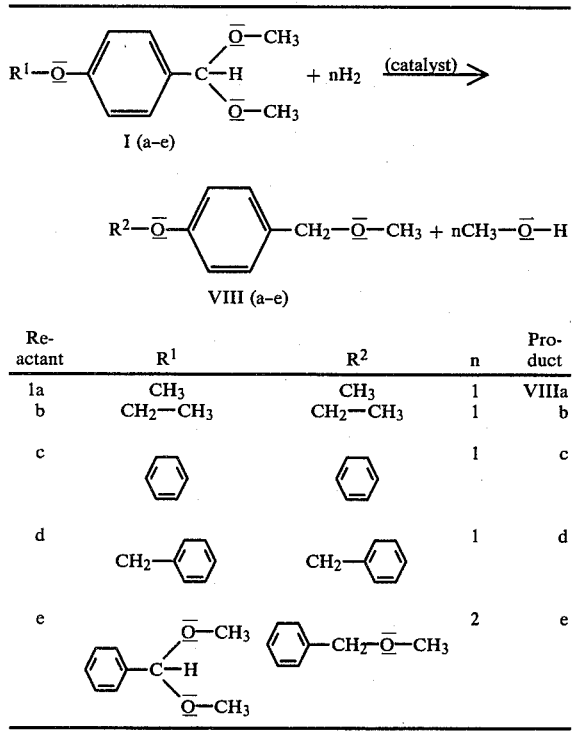

The principal products being formed in the process according to the invention either contain the uncharged radical R of the reactant (in this case, $R^1=R^2$ in the general equation and in the table) or—if the radical R itself carries a hydrogenolyzing group, such as a dimethylacetal group—they contain a radical R′ which has been changed with respect to R (in this case, $R^1\neq R^2$ in the general equation and in the table).

Among the compounds listed, the reactants (Ia), (Ic) and (Ie) are particularly preferred.

The nitrogen-containing heterocyclic compounds to be employed in the process according to the invention include, in particular, pyridine, pyrrole, pyrrolidone and piperidine, wherein pyridine has proved to be particularly suitable. These heterocyclic compounds can be employed individually or as a mixture. By adding these heterocyclic compounds in the process according to the invention together with the known cobalt carbonyl catalyst (it being assumed in general that the latter can be present in the reaction system, inter alia, in the form of $Co_2(CO)_8$, $Co(CO)_4$ and/or $HCo(CO)_4$), the selectivity of the catalyst system in the transformation of the aldehyde-acetal group or groups into a methoxymethyl group or groups is decisively improved, i.e., in the hydrogenolysis, both the benzyl ether cleavage and the insertion reaction of carbon monoxide are suppressed. This selectivity control is extremely surprising since, as demonstrated in the description of the state of the art, the known addition of phosphorus compounds fails completely in this case, and even the known "base reaction" would actually have suggested away from an addition of the nitrogen-containing heterocyclic compounds. In the process according to the invention, however, the addition of the heterocyclic compounds does not entail a disproportionation of the cobalt carbonyl.

The nitrogen-containing heterocyclic compounds improve the selectivity of the cobalt carbonyl catalyst even at a molar ratio of the heterocyclic compound to cobalt (relative to the cobalt proportion in the cobalt carbonyl) of about 1:1, so that they can virtually be regarded as co-catalysts. The proportion of the heterocyclic compounds can be increased up to about 16:1, and a range of from about 2:1 to 4:1 is preferred.

Advantageously, the process according to the invention is carried out in methanol as an organic solvent, but other organic solvents, such as tetrahydrofuran (THF), are also suitable. Since methanol is formed in the course of the reaction, methanol is particularly suitable as the organic solvent, in particular since it can then be re-used in further batches, after a simple distillation. The proportion of the acetal which is to be hydrogenolyzed in the system is of rather subordinate importance. Advantageously it should be in the range from about 10 to 80% by weight; however, 40 to 60% strength by weight solutions are preferred since they are particularly easy to handle.

An important factor for a rapid and selective course of reaction is the concentration of the cobalt carbonyl catalyst (calculated as the Co proportion in the mononuclear complex), relative to the dimethylacetal group to be hydrogenolyzed. This concentration is between about 0.5 and 5 mole %, in particular between about 0.75 and 2 mole %, per mole of dimethylacetal group. If less than 0.5 mole % of cobalt carbonyl catalyst is employed, the reaction proceeds too slowly; whereas, at a concentration of more than 5 mole %, the carbonylation of, for example, the preferred organic solvent methanol begins to be catalyzed to a measurable extent.

The catalyst system is essentially made up of the three components (a) cobalt carbonyl, (b) the nitrogen-containing base, and (c) the carbon monoxide. An advantageous combined action of these components is obtained with the following proportions: from about 0.5 to 5 mole %, in particular from about 0.75 to 2 mole %, of (a), from about 0.5 to 20 mole %, in particular from about 1.5 to 8 mole %, of (b), each relative to 1 mole of dimethylacetal group, and from about 20 to 60 bar, in particular from about 30 to 50 bar, of carbon monoxide partial pressure. The carbon monoxide is necessary for stabilizing the homogeneous catalyst system at the relatively high reaction temperature of about 115° to 150° C., in particular from about 125° to 135° C. Higher carbon monoxide partial pressures are of little advantage since, in that case, carbon monoxide is also increasingly inserted into the dimethylacetal group in a side reaction (homologation). For the actual hydrogenolysis of the reactants, only hydrogen is consumed so that, in the course of the reaction with falling pressure, only hydrogen needs to be added regularly (re-injected). The hydrogen partial pressure in the process according to the invention can be varied within a wide range, with about 20 bar to be regarded as the lower limit, while 200 bar can be taken as an appropriate upper limit. Preferably, the process is carried out at a hydrogen partial pressure of from about 80 to 120 bar, so that the hydrogenolysis can be carried out at a total system pressure of less than about 200 bar. These partial pressure data or pressure data are based on a temperature of about 20° C., and they rise with an increase in temperature.

By way of example, the general conditions of the process according to the invention are further explained below. The first step of the process comprises the introduction or preparation of a solution of cobalt carbonyl in the pressure reactor. In the case of relatively small batches, it may be entirely appropriate to prepare a solution of pure solid cobalt carbonyl in methanol or in another organic solvent and then to use this solution in the reaction. In the case of larger batches, however, it is better to use a procedure in which the solution of cobalt carbonyl is produced from a compound, containing cobalt in the divalent form, in the organic solvent, with addition of carbon monoxide/hydrogen under pressure at an elevated temperature, either in the hydrogenation reactor itself or in a separate pressure reactor. Cobalt compounds suitable for this procedure are, inter alia, cobalt formate, cobalt acetate or cobalt 2-ethylhexanoate which readily react at temperatures of 100° to 140° C. to give cobalt carbonyl, for example, in solution in methanol and under a partial pressure of 50 to 200 bar of carbon monoxide to which varying amounts of hydrogen can be admixed for an improved reduction. The solution of the co-catalyst can then be added to the solution of the cobalt carbonyl; however, the nitrogen-containing heterocyclic compound can also be introduced into the reaction mixture at a later stage, together with the dimethylacetal which is to be hydrogenolyzed.

The dimethylacetal is, as a rule, added to the catalyst solution at room temperature and without pressure, particularly if the process according to the invention is carried out discontinuously. In the case of a continuous reaction, however, the dimethylacetal must be pumped by means of a metering pump into the reaction mixture present in the reactor, against the elevated reaction pressure. The actual reaction time depends very strongly on the other reaction conditions indicated above. For example, reaction times of about 0.3 to 5 hours are appropriate in order to realize an effective conversion of the dimethylacetals introduced.

When the hydrogenolysis has ended, the excess gas mixture is evacuated, and the clear yellow solution is removed from the pressure reactor and transferred into a reaction vessel, for example, a glass sphere with a stirrer, which is suitable for destroying the cobalt carbonyl. The destruction of the cobalt carbonyl is effected by adding a sufficient quantity of an acid, with simultaneous introduction of air. Furthermore, it can be advantageous to warm this reaction mixture to about 60° C. Formic acid, oxalic acid or phosphoric acid are particularly suitable as acids for precipitating the oxidatively formed $Co^{2+}$ ions in the form of the corresponding salt. The $Co^{2+}$ salt which has precipitated is filtered off, and the filtrate essentially contains a solution of the resulting p-substituted benzyl methyl ether in the organic solvent, which solution is, however, still slightly contaminated with by-products. The types and proportions of the by-products will be indicated in more detail in the examples which follow.

Since not only by-products with a relatively lower boiling point than that of the main product, but also higher-molecular fractions which cannot be distilled can be present in the reaction mixture, the working-up of the latter also comprises the following steps: (a) separating off the organic solvent (which advantageously is re-used in new reaction batches) by distillation, (b) thin-layer distillation of the residue from (a) under a reduced pressure of about 0.1 to 7 mbar in order to separate off the products, which can be distilled, from higher-molecular products, and (c) an alkaline purification of the distillate obtained under (b), the distillate being extracted while hot, for example, with 3 to 20% strength by weight sodium hydroxide solution, in order to remove the by-products containing acid groupings, such as methyl carboxylates, from the crude product (distillate). The crude product worked up in this way then contains only defined compounds to the extent of more than about 95% by weight, and the main fraction thereof represents the desired p-substituted benzyl methyl ether, which can be isolated, in a high purity of more than 99% by weight, from this crude product by a column distillation in vacuo.

The process according to the invention, with a high degree of refining, opens up a new route, for example, for the preparation of diethers or triethers with an aromatic core portion, for example, to the industrially important compound (VII)=(VIIIe), namely, 4,4'-bis-methoxymethyl-diphenyl ether. This compound is of particular importance in the preparation of aromatic polyethers from hydroxymethyl diaryl ethers or alkoxymethyl diaryl ethers. (See, for example, German Pat. No. 1,252,903 or U.S. Pat. No. 3,316,186) These aromatic polyethers are suitable as binders in the preparation of casting compositions or as an adhesive in the production of laminates. Another known use of this compound is its reaction (described in German Offenlegungsschrift No. 2,065,732=U.S. Pat. No. 3,867,147) with aromatic diazonium compounds to give light-sensitive condensation products from these two components.

In the examples which follow, % data are by weight, unless otherwise stated. Parts by weight have the same relationship to parts by volume as the g to the $cm^3$.

EXAMPLE 1

The reaction is carried out in a "V4A" steel pressure reactor which has a maximum capacity of 200 parts by volume and which can be adjusted to a given temperature. Mixing of the reaction mixture is effected by means of a magnetic stirrer. Through a bore in the cover, which is closed during the pressure reaction, it is possible, in the unpressurized state, to add liquid substances to the reaction mixture or to take samples from the latter, in order to enable the course of the reaction to be monitored and controlled in this way.

The example starts with the formation of cobalt carbonyl. A solution of 1.5 parts by weight of cobalt 2-ethyl-hexanoate (Co content 16%, corresponding to 0.24 part by weight or 0.004 atom part by weight of Co) in 50 parts by volume of methanol is introduced into the reactor. Under a pressure of 200 to 240 bar of a $CO/H_2$ mixture in a ratio of 1:1, the reactor is warmed to 130° C., the formation of carbonyl proceeding rapidly and quantitatively after a certain induction period. The pressure of the reactor is then reduced and the reactant together with the co-catalyst is introduced: 36.4 parts by weight of 4-methoxybenzaldehyde-dimethylacetal, diluted with 30 parts by volume of methanol, and 0.66 part by volume (=0.63 part by weight) of pyridine are employed. The molar proportions of the components are then 2 mole % of cobalt carbonyl and 4 mole % of pyridine per mole of dimethylacetal group. Subsequently, a CO/$H_2$ mixture is again injected. The carbon monoxide partial pressure is 40 bar and the hydrogen partial pressure is about 80 bar. The two values are determined at about 20° C., and the reaction itself proceeds at about 130° C., with the pressure in the reactor rising to a maximum of about 160 bar. The course of the reaction can be clearly followed by the pressure drop (decrease in hydrogen), and after a reaction time of about 20 minutes, the reaction is stopped by rapid cooling. After cooling to room temperature is complete, the gas mixture which is still present in excess is evacuated, and the reaction solution is removed from the pressure reactor.

To destroy the cobalt carbonyl, 1.46 parts by weight of formic acid are added to the reaction solution and the latter is warmed to about 60° C. while air is passed therethrough. About 70 to 80% of the Co formate formed crystallizes out and can readily be filtered off. The filtrate obtained is free from cobalt carbonyl, and the organic solvent methanol is removed from the filtrate in a rotary evaporator. The remaining crude product is analyzed by gas chromatography (carrier gas: He, standard: phenoxytoluene). The proportions obtained relate to 100% conversion, and they can be seen in the table which follows.

EXAMPLES 2 AND 3 AND COMPARATIVE EXAMPLES V 1 AND V 2

The procedure indicated in Example 1 is followed but with the use of varying amounts of the co-catalyst pyridine, or without any co-catalyst (see table). The results of the examples according to the invention and of the comparative examples show significantly the influence of the co-catalyst on the relative yield of p-substituted benzyl methyl ether.

| Example | 1 | 2 | 3 | V 1 | V 2 |
|---|---|---|---|---|---|
| Mole % of cobalt carbonyl | 2 | 2 | 2 | 2 | 2 |
| Mole % of pyridine | 4 | 2 | 8 | — | — |
| CO partial pressure in bar | 40 | 40 | 40 | 40 | 40 |
| $H_2$ partial pressure in bar | 80 | 80 | 80 | 80 | 80 |
| Reaction temperature in °C. | 130 | 130 | 130 | 130 | 120 |
| Reaction time in minutes | 20 | 20 | 30 | 20 | 15 |
| Conversion of the reactant in % | 100 | 100 | 88 | 100 | 92 |
| Selectivity in % (recalculated to 100% conversion of the reactant) to | | | | | |
| $H_3C-\underline{O}-\langle\rangle-CH_2-\underline{O}-CH_3$ 4-methoxybenzyl methyl ether | 84 | 68 | 97 | 10 | 12 |
| $H_3C-\underline{O}-\langle\rangle-CH_3$ 4-methoxytoluene | 6 | 6 | 1 | 49 | 49 |
| $H_3C-\underline{O}-\langle\rangle-CH_2-CH(\underline{O}-CH_3)_2$ (4-methoxyphenyl)-acetaldehyde-dimethylacetal | 10 | 26 | 1 | 40 | 38 |

EXAMPLE 4 AND COMPARATIVE EXAMPLE V 3

The procedure indicated in Example 1 is followed, but 32 parts by weight of 4,4'-diphenyl ether-dialdehyde-bis-dimethylacetal are used as the reactant. The molar proportions of the components are thus likewise 2 mole % of cobalt carbonyl and 4 mole % of pyridine per mole of dimethylacetal group. The reaction itself is carried out at about 130° to about 135° C., and the reaction time is 150 minutes. In Comparative Example V 3, the pyridine is omitted under otherwise identical conditions. With 100% conversion of the reactant, the following products are obtained with the selectivities given below (determined by gas chromatography):

| Product | Selectivity in Example | |
|---|---|---|
| | 4 | V 3 |
| 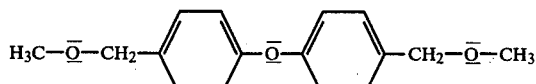<br>4,4'-bis-(methoxymethyl)-diphenyl ether | 93.0% | 26.0% |
| 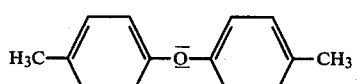<br>4,4'-dimethyl-diphenyl ether | 0.5% | 7.1% |
| 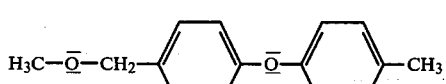<br>4-methoxymethyl-4'-methyl-diphenyl ether | 3.5% | 15.7% |
| 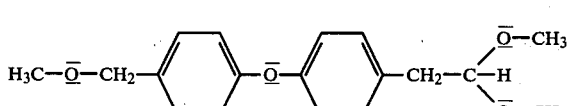<br>4-methoxymethyl-4'-dimethoxyethyl-diphenyl ether | 2.3% | 19.7% |

In Comparative Example V 3, a number of further by-products are also obtained which, in Example 4 according to the invention, are detectable only in traces or not at all.

EXAMPLE 5

The importance of the addition of pyridine in order to increase the selectivity manifests itself particularly clearly when the reactant used is crude 4,4'-diphenyl ether-dialdehyde-bis-dimethylacetal instead of a product which has been purified by distillation. This reactant is obtained in the crude form after the electro-chemical methoxylation of 4,4'-dimethyldiphenyl ether (see the introductory part of the description, relating to the state of the art), and intermediate purification can frequently be a disadvantage in largescale industrial processes since, at the least, it is expensive.

The pressure reactor has a maximum capacity of 2,000 parts by volume, and 15 parts by weight of cobalt 2-ethyl-hexanoate (corresponding to 2.4 parts by weight or 0.04 atom part by weight of Co) in 500 parts by volume of methanol are introduced. The CO/H₂ mixture is injected up to a pressure of about 200 bar and the batch is warmed to about 135° C. As the reactant, 640 parts by weight of the crude bis-dimethylacetal in 300 parts by volume of methanol and 6.34 parts by weight of pyridine are added. A gas mixture under a CO partial pressure of 40 bar and an H₂ partial pressure of 80 bar is injected into the reaction mixture and, on warming to about 130° C., the pressure reaches a value of about 155 bar. About 40 minutes after the start of the reaction, the pressure has fallen to about 100 bar, and H₂ is re-injected up to a total pressure of 160 bar. After a further 180 minutes, the pressure has fallen to about 120 bar, and the reaction has ended. To destroy the cobalt carbonyl, 14.6 parts by weight of formic acid are added to the cooled reaction mixture. After the organic solvent methanol has been separated off, there is obtained 580 parts by weight of a crude product which is subjected to thin-layer distillation under 0.3 mbar and at a temperature of the evaporator of 190° C., with 503 parts by weight of distillate and 70 parts by weight of an undistillable residue being obtained. The subsequent distillation through a column is facilitated if the distillate from the thin-layer distillation is additionally extracted with an approximately equal volume of 10% strength aqueous NaOH solution at 100° C. Carboxylic acids, their methyl esters and other by-products having an acid character are separated off by this intermediate purification. The subsequent fractional distillation gives 52 parts by weight of light ends at about 84° to 204° C. (vacuum 6.5 mbar) and 382 parts by weight of a main fraction at 204° C. The compositions are as follows:

Light ends:
- 7 parts by weight of 4,4'-dimethyl-diphenyl ether (=2%)
- 31 parts by weight of 4-methoxymethyl-4'-methyl-diphenyl ether (=8%)
- 14 parts by weight of 4,4'-bis-(methoxy-methyl)-diphenyl ether (=3%)

Main fraction: 382 parts by weight of 4,4'-bis-(methoxy-methyl)-diphenyl ether (=85%)

Only a very small distillation residue remains, and the desired main product is colorless and does not discolor even on prolonged standing.

COMPARATIVE EXAMPLE V 4

The procedure indicated in Example 5 is followed, but without the addition of the co-catalyst pyridine. The reaction is carried out under the same gas pressure, but at 125° C. (instead of 130° C. in Example 5). The reaction has already ended after 90 minutes, i.e., the reactant has been completely converted after this time. After the organic solvent has been separated off, 550 parts by weight of a crude product remain, in which 21% of 4,4'-bis-(methoxymethyl)-diphenyl ether are detected by gas chromatographic analysis. The thin-layer distillation of this crude product gives 440 parts by weight of distillate and an increased proportion of 105 parts by weight of an undistillable residue. The subsequent NaOH extraction takes a course different from that of Example 5, since solid products are formed which, because they cause interference, accumulate at the liquid/liquid phase boundary and make phase separation virtually impossible. The latter becomes possible only after an auxiliary solvent, such as toluene, has been added, but this must be removed again by distillation, at extra cost. The fractional distillation of the product, which has undergone an intermediate purification in this way, gives 132 parts by weight of a first fraction in a range from about 59° to 179° C. (vacuum 2.6 mbar), 90 parts by weight of a second fraction in a range from about 162° to 164° C. (vacuum 1.3 mbar) and 125 parts by weight of a last fraction in a range from about 165° to 192° C. (vacuum 1.3 mbar), in addition to some resinous residues. The compositions are as follows:

1st fraction:
  parts by weight of 4,4'-dimethyl-diphenyl ether (8%)
  91 parts by weight of 4-methoxymethyl-4'-methyl-diphenyl ether (25%)
  12 parts by weight of 4,4'-bis-(methoxymethyl)-diphenyl ether (2%)
2nd fraction:
  87 parts by weight of 4,4'-bis-(methoxymethyl)-diphenyl ether (19%)
3rd fraction:
  24 parts by weight of methyl 4-(4'-methoxymethyl-phenoxy)-benzoate (5%)
  73 parts by weight of 4-methoxymethyl-4'-dimethoxyethyl-diphenyl ether (15%)
and further components of unknown composition. The isolated 4,4'-bis-(methoxymethyl)-diphenyl ether thus amounts to only about 19% of the theoretical yield. In amounts to only about 19% of the theoretical yield. In addition, it still contains impurities which lead to a yellow coloration, even after distillation.

EXAMPLE 6

The procedure indicated in Example 1 is followed, except there is used 0.75 part by weight of cobalt 2-ethyl-hexanoate (corresponding to 0.002 atom part by weight of Co), 300 bar of H₂/CO mixture in the stage of preparing the cobalt carbonyl, 25 parts by weight of 4-phenoxybenzaldehyde-dimethylacetal and 0.33 part by volume of pyridine. The molar proportions of the components are then 2 mole % of cobalt carbonyl and 4 mole % of pyridine per mole of dimethylacetal group. After a hydrogenolysis reaction time of about 60 minutes, a further 20 bar of H₂ is injected, and the total reaction time is about 120 minutes, with the conversion of the reactant amounting to 100%. According to analysis by gas chromatography and working up by distillation, the crude product obtained is composed of:

92% of 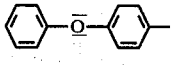 (4-phenoxybenzyl) methyl ether,

1% of 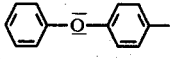 4-phenoxytoluene,

4% of further by-product, and
3% of undistillable components.

What is claimed is:
1. A process for the catalytic hydrogenolysis of p-substituted benzaldehyde-dialkylacetals to produce the corresponding p-substituted benzyl alkyl ether derivatives, comprising the step of:
  hydrogenolyzing a p-substituted benzaldehyde-dialkylacetal compound selected from the group consisting of 4-methoxy-benzaldehyde-dimethylacetal, 4-phenoxy-benzaldehyde-dimethylacetal, and 4,4'-diphenyl ether-dialdehydebis-dimethylacetal, in the presence of a catalyst system comprising a cobalt carbonyl and at least one heterocyclic compound containing at least one heterocyclic nitrogen atom selected from the group consisting of pyridine, pyrrole, pyrrolidone and piperidine.
2. A process as claimed in claim 1, wherein the molar ratio of said nitrogen-containing heterocyclic compound to said cobalt carbonyl is in the range of from 1:1 to 16:1.
3. A process as claimed in claim 2, wherein the concentration of said cobalt carbonyl is between about 0.5 and 5 mole % per mole of dimethylacetal group.
4. A process as claimed in claim 3, wherein the proportion of said cobalt carbonyl is from about 0.5 to 5 mole % and the proportion of said nitrogen-containing heterocyclic compound is from about 0.5 to 20 mole %, each relative to 1 mole of dimethylacetal group, and the carbon monoxide partial pressure is from about 20 to 60 bar.
5. A process as claimed in claim 4, wherein the proportion of said cobalt carbonyl is from about 0.75 to 2 mole % and the proportion of said nitrogen-containing heterocyclic compound is from about 1.5 to 8 mole %, each relative to 1 mole of dimethylacetal group, and the carbon monoxide partial pressure is from about 30 to 50 bar.

* * * * *